(12) United States Patent
Ikeda et al.

(10) Patent No.: US 12,004,747 B2
(45) Date of Patent: Jun. 11, 2024

(54) TISSUE-JOINING MEMBER, AND USE THEREOF

(71) Applicant: Tetsuo Ikeda, Fukuoka (JP)

(72) Inventors: Tetsuo Ikeda, Fukuoka (JP); Shun Sasaki, Fukuoka (JP); Eiji Oki, Fukuoka (JP); Shinichiro Okihara, Shizuoka (JP)

(73) Assignee: IKEDA, TETSUO, Fukuoka (JP)

( * ) Notice: Subject to any disclaimer, the term of this patent is extended or adjusted under 35 U.S.C. 154(b) by 954 days.

(21) Appl. No.: 16/977,350

(22) PCT Filed: Feb. 26, 2019

(86) PCT No.: PCT/JP2019/007317
§ 371 (c)(1),
(2) Date: Sep. 1, 2020

(87) PCT Pub. No.: WO2019/167943
PCT Pub. Date: Sep. 6, 2019

(65) Prior Publication Data
US 2021/0106332 A1    Apr. 15, 2021

(30) Foreign Application Priority Data
Mar. 2, 2018 (JP) .................. 2018-037082

(51) Int. Cl.
*A61B 17/08* (2006.01)
*A61L 31/04* (2006.01)
(Continued)

(52) U.S. Cl.
CPC .......... *A61B 17/085* (2013.01); *A61L 31/044* (2013.01); *A61L 31/14* (2013.01); *A61N 5/067* (2021.08)

(58) Field of Classification Search
CPC ..... A61B 17/085; A61L 31/044; A61L 31/14; A61N 5/067
See application file for complete search history.

(56) References Cited

U.S. PATENT DOCUMENTS

| | | |
|---|---|---|
| 4,233,360 A | 11/1980 | Luck et al. |
| 5,618,551 A | 4/1997 | Tardy et al. |

(Continued)

FOREIGN PATENT DOCUMENTS

| | | |
|---|---|---|
| JP | H4-231961 A | 8/1992 |
| JP | H7-59812 A | 3/1995 |

(Continued)

OTHER PUBLICATIONS

Ghanaati et al., "Bilayered, non-cross-linked collagen matrix for regeneration of facial defects after skin cancer removal: a new perspective for biomaterial-based tissue reconstruction", J. Cell Commun. Signal., 10, 2016, pp. 3-15.

(Continued)

*Primary Examiner* — Ashley L Fishback
(74) *Attorney, Agent, or Firm* — Greenblum & Bernstein, P.L.C.

(57) ABSTRACT

This tissue-joining member comprises non-crosslinked fibrous collagen. A laminate body comprises: a support; a joining member that is layered on one surface of the support; and a first adhesive layer that is layered on said one surface of the support in a region on which the joining member is not layered. The method for using the joining member or the laminate body comprises: a heating step in which the joining member or the laminate body is heated to less than 60° C. and greater than body temperature after having being layered on the tissue; and a cooling step in which the heated joining member or laminate body is cooled to body tem- (Continued)

perature or lower. A treatment system comprises a heating unit and the joining member or the laminate body.

13 Claims, 7 Drawing Sheets

(51) Int. Cl.
*A61L 31/14* (2006.01)
*A61N 5/067* (2006.01)

(56) References Cited

U.S. PATENT DOCUMENTS

| | | | |
|---|---|---|---|
| 6,623,963 B1* | 9/2003 | Muller | A61L 27/3612 623/23.72 |
| 2006/0159731 A1* | 7/2006 | Shoshan | A61K 38/39 424/443 |
| 2007/0034667 A1 | 2/2007 | Holsten et al. | |

FOREIGN PATENT DOCUMENTS

| | | |
|---|---|---|
| JP | H8-33700 A | 2/1996 |
| JP | 2002-524110 A | 8/2002 |
| JP | 2018-020149 A | 2/2018 |
| WO | WO 1992/13578 A1 | 8/1992 |
| WO | WO 2000/09018 A1 | 2/2000 |

OTHER PUBLICATIONS

Ghanaati, "Non-cross-linked porcine-based collagen I-III membranes do not require high vascularization rates for their integration within the implantation bed: A paradigm shift", Acta Biomaterialia, 8, 2012, pp. 3061-3072.
Doillon et al., "Bioactive collagen sponge as connective tissue substitute", Materials Science and Engineering C2, 1994, pp. 43-49.
Sasaki et al., "Elucidation of the mechanism of thermal fusion of collagen tissue and development of new biomaterial collagen tissue coaptation techniques", The 118th Annual Congress of Japan Surgical Society, 2018 (w/ translation).
ISR for PCT/JP2019/007317, dated Jun. 4, 2019.
Written Opinion of the ISA for PCT/JP2019/007317, dated Jun. 4, 2019 (w/ translation).
EESR for EP App. No. 19760210.5, dated Sep. 28, 2021.
Reddy et al., "Thermosensitive Transparent Semi-Interpenetrating Polymer Networks for Wound Dressing and Cell Adhesion Control", Biomacromolecules, 9(4):1313-1321 (2008).

* cited by examiner

[Fig. 1]
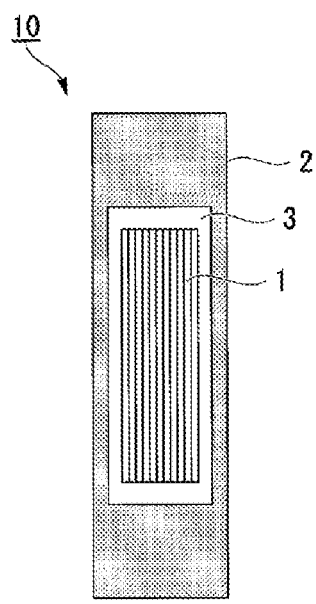
[Fig. 2]
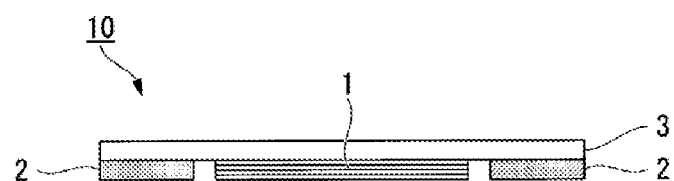

[Fig. 3]
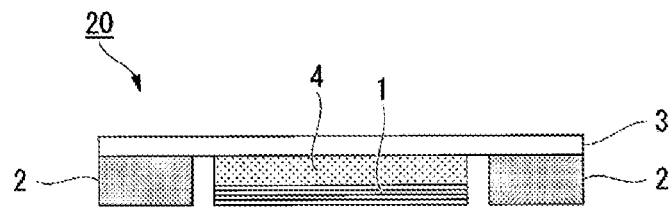
[Fig. 4]
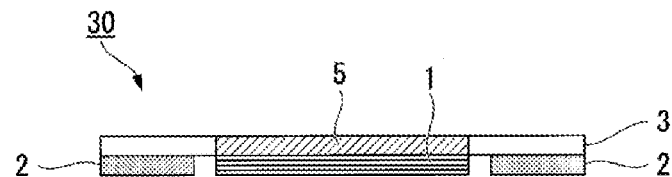
[Fig. 5]
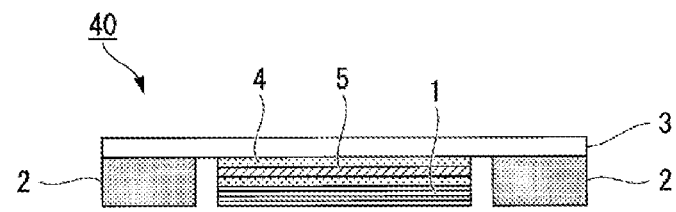

[Fig. 6]
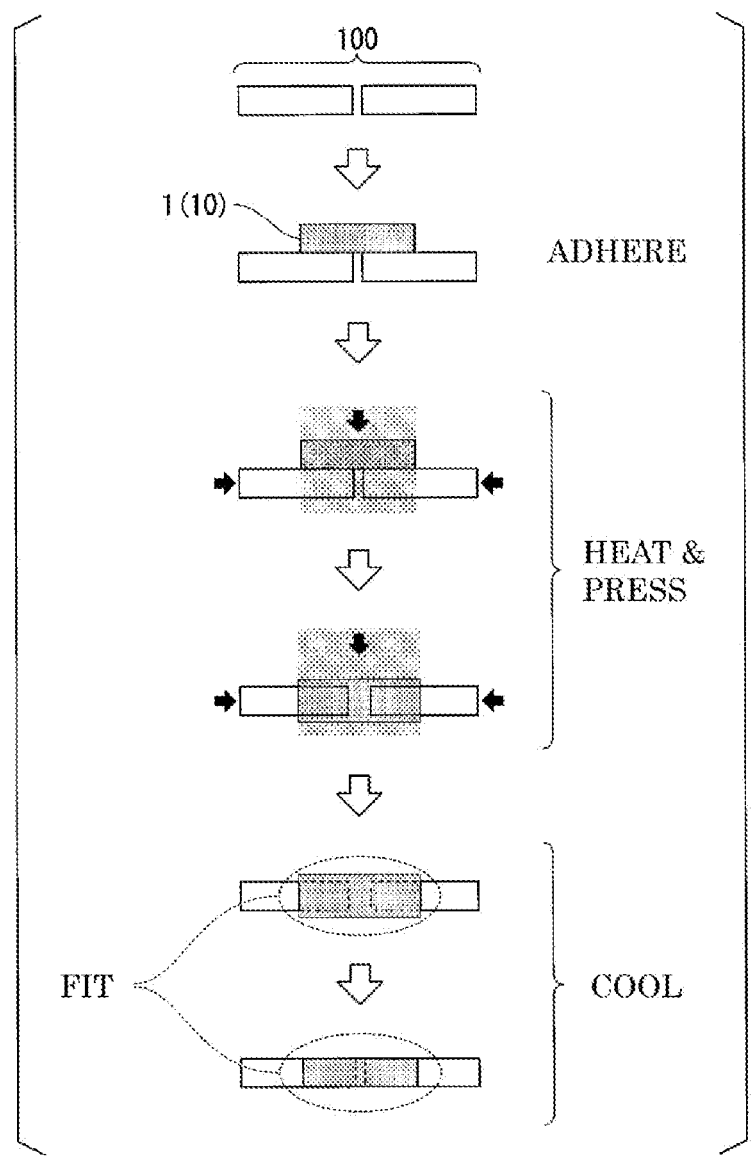

[Fig. 7]
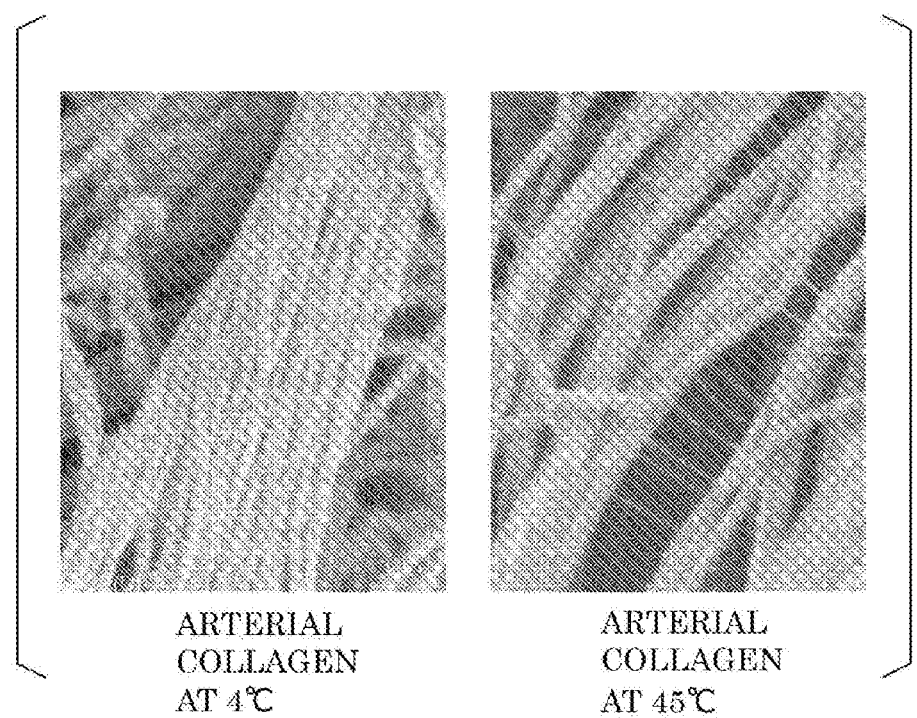

[Fig. 8]
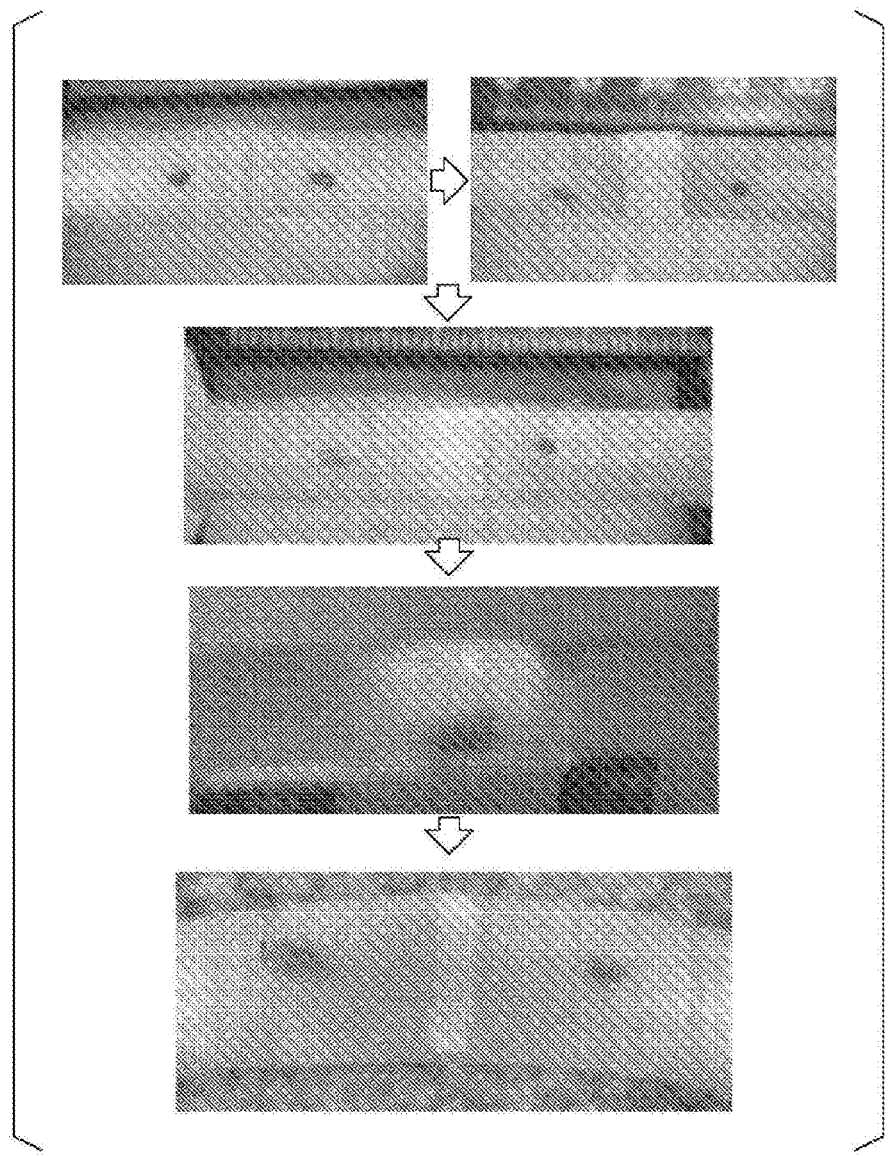

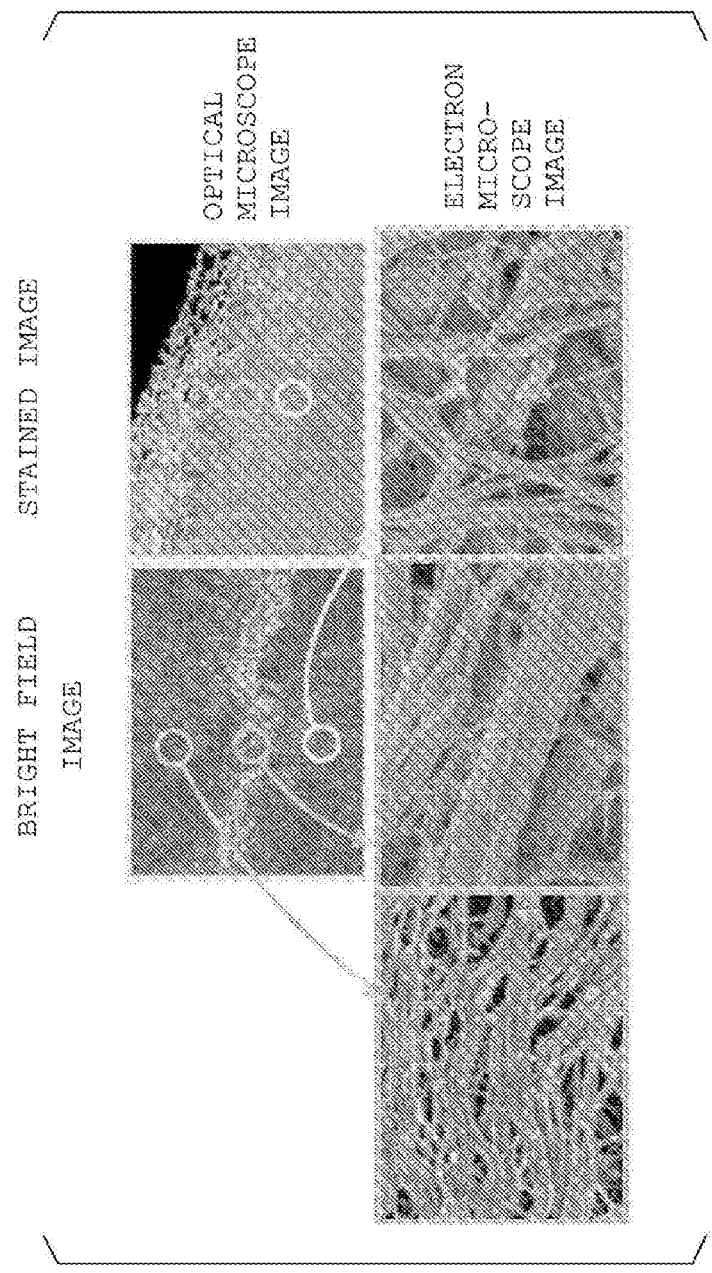
[Fig. 9]

[Fig.10]
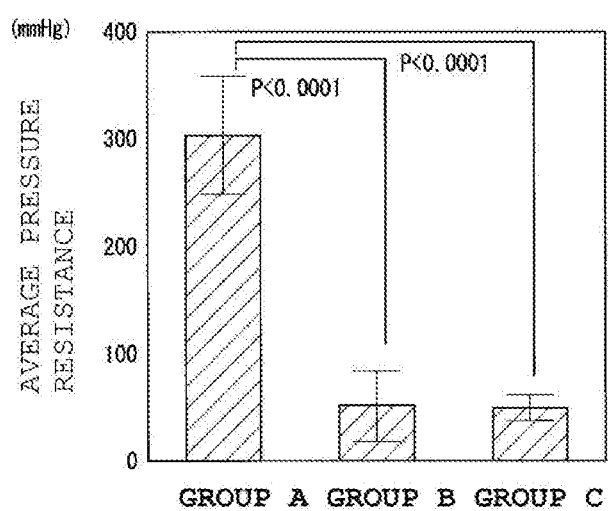

TISSUE-JOINING MEMBER, AND USE THEREOF

TECHNICAL FIELD

The present invention relates to a tissue-joining member and use thereof. Specifically, the present invention relates to a tissue-joining member, a laminate body, a using method thereof, and a treatment system. The present application claims priority based on Japanese Patent Application No. 2018-037082 filed in Japan on Mar. 2, 2018, the contents of which are incorporated by reference herein.

BACKGROUND ART

Examples of a conventional method for joining a living tissue include a suture method using a thread, a method using a staple (for example, see Patent Literature 1), a press-bonding method, and the like.

Conventional joining methods may result in tissue disorders such as cutting, crushing, dehydration, and carbonization of a tissue due to penetration of a suture needle or staple needle, excessive pressure, and heating.

CITATION LIST

Patent Literature

Patent Literature 1: Japanese Patent Laid-Open No. 2018-020149

SUMMARY OF INVENTION

Technical Problem

The present invention has been made in view of the circumstances, and provides a technique for joining a living tissue without causing tissue disorders.

Solution to Problem

As a result of intensive studies to achieve the object, the inventors have found that fibers are loosened and expanded by heating collagen fibers in a living tissue to a temperature higher than body temperature. In addition, it has been found that loosened fibers contract and return to an original state by lowering the temperature of expanded collagen fibers to body temperature or lower.

Further, it has been found that, by press-bonding a member containing fibrous collagen to collagen fibers in a living tissue and heating to a temperature higher than body temperature, the collagen fibers in the living tissue and the fibrous collagen in the member are loosened and expanded, and the fibers are entangled with each other, subsequently, by lowering the temperature to body temperature or lower, the loosened fibers contract and fit in a entangled state, and the two can be firmly joined, and the present invention has been completed.

The invention includes following aspects.

A tissue-joining member according to a first aspect of the invention comprises a non-crosslinked fibrous collagen.

The joining member of the above-mentioned first aspect may be film-like, sheet-like, or sponge-like.

The joining member of the above-mentioned first aspect substantially may not comprise water.

According to the joining member of the above-mentioned first aspect, the non-crosslinked fibrous collagen may be an atelocollagen.

A laminate body according to a second aspect of the invention, comprises:
 a support;
 a joining member according to the first aspect of the joining member, which is layered on one surface of the support; and
 a first adhesive layer that is layered on said one surface of the support in a region on which the joining member is not layered.

The laminate body of the above-mentioned second aspect may comprise a second adhesive layer that is layered between the support and the joining member.

According to the laminate body of the above-mentioned second aspect, the support or the second adhesive layer comprises a temperature-sensitive material at least in part thereof.

A using method according to a third aspect of the invention, which is the method using the joining member of the first aspect or the laminate body of the second aspect, comprises:
 a heating step in which the joining member or the laminate body is heated to less than 60° C. and greater than body temperature after having being layered on the tissue; and
 a cooling step in which the heated joining member or laminate body is cooled to body temperature or lower.

A treatment system according to a fourth aspect of the invention, comprises the joining member according to the first aspect or the laminate body according to the second aspect; and
 a heating unit. The treatment system according to the above-mentioned fourth aspect may comprise further a temperature control unit configured to control the heating unit such that a temperature of the joining member or the laminate body heated by the heating unit is less than 60° C. and greater than body temperature.

According to the treatment system of the above-mentioned fourth aspect, the heating unit may be a laser.

Advantageous Effects of Invention

According to any one of the above-mentioned aspects of the tissue-joining member, the laminate body, the method using thereof, and the treatment system, a live tissue can be joined without causing tissue disorders.

BRIEF DESCRIPTION OF DRAWINGS

FIG. 1 is a bottom view showing an example of a laminate body of the present embodiment.

FIG. 2 is a cross-sectional view showing an example of the laminate body of the present embodiment.

FIG. 3 is a cross-sectional view showing an example of a laminate body of the present embodiment.

FIG. 4 is a cross-sectional view showing an example of a laminate body of the present embodiment.

FIG. 5 is a cross-sectional view showing an example of a laminate body of the present embodiment.

FIG. 6 is a schematic process view showing an example of a method for using a joining member or a laminate body of the present embodiment.

FIG. 7 is electron microscope images showing an arterial collagen at 4° C. and 45° C. in Reference Example 1.

FIG. 8 is a diagram showing a procedure for joining a bovine carotid artery using a laminate body in Example 1.

FIG. 9 is an optical microscope image and an electron microscope image of the joined bovine carotid artery (Group A) in Example 1.

FIG. 10 is a graph showing results of a pressure resistance test of the joined bovine carotid artery in Example 1.

DESCRIPTION OF EMBODIMENTS

<<Tissue-Joining Member>>

A tissue-joining member of the present embodiment (hereinafter it may be simply referred to as "joining member") contains a non-crosslinked fibrous collagen.

In the joining member of the present embodiment, by heating to about less than 60° C. and greater than body temperature, the non-crosslinked fibrous collagen can be relaxed and expanded as shown in the examples below. Therefore, in the heating state, a phenomenon called fitting occurs, in which thin collagen fibers are entangled with each other, by pressing the non-crosslinked fibrous collagen of the joining member of the present embodiment in close contact with the collagen fibers in a living tissue. In addition, by lowering the temperature again to about body temperature or lower, the collagen fibers can contract and tighten while the collagen fibers are still fitted, and the collagen fibers can be brought into a bonded state. In addition, at a temperature less than 60° C. and greater than body temperature, denaturation and destruction of tissue components (in particular, proteins and the like) of a living tissue are unlikely to occur. Therefore, by using the joining member of the present embodiment, it is possible to join a living tissue without causing a tissue disorder such as denaturation and destruction of tissue components of the living tissue. That is, a living tissue can be joined without bleeding, hardening, dehydration, carbonization or the like caused by tissue damage. In addition, the joining member of the present embodiment has an effect of hemostasis at a joined portion of a living tissue, and an effect of preventing leakage of bodily fluids such as bile, pancreatic fluid and lymphatic fluid, and leakage of gas such as lung leakage.

Further, in general, "collagen" is one of proteins mainly constituting dermis, ligaments, tendons, bones, cartilage and the like of vertebrates, and is a main component of an extracellular matrix of a multicellular animal. In addition, an amino acid residue constituting a peptide chain of a collagen protein has a primary structure of "-G (glycine residue) -X (amino acid X) -Y (amino acid Y)" (where X and Y each independently represent an arbitrary amine acid residue), in which glycine residues repeat every three residues. In addition, one peptide chain constituting the collagen protein is referred to as an α-chain. In a collagen, three α-chains are gathered in a manner shifted by one amino acid residue respectively and the glycine residues come to the center, so as to form a loose right-handed helical structure. Further, hereinafter, this helical structure may be referred to as "collagen molecule".

In addition, "fibrous collagen" or "collagen fiber" means that the collagen molecules are gradually displaced and gathered in large numbers to form fibers, and a thickness thereof is about several tens of nm or more and hundreds of nm or less. "Fibrous collagen" or "collagen fiber" may be referred to as "collagen fibril".

In the present description, "collagen fiber bundle" means a structure in which several hundreds of thousands or more and several millions or less of the collagen fibers are bundled, and the thickness thereof is about several μm or more and several tens of μm or less. The "collagen fiber bundle" may be referred to as "collagen fiber".

In addition, in the present description, "denaturation" means that a three-dimensional structure is clearly and irreversibly changed even if the amino acid sequence of the protein is unchanged. As described above, expanding of the fibrous collagen is a minor change, which corresponds to a change in a quaternary structure of the protein and is highly likely to be reversible. Therefore, "denaturation" in the present description does not include expanding of the fibrous collagen.

<Fibrous Collagen>

The joining member of the present embodiment contains a non-crosslinked fibrous collagen as a main component.

In the present specification, "non-crosslinked fibrous collagen" refers to fibrous collagen that is not crosslinked or has no crosslinking groups.

In addition, the fibrous collagen includes non-crosslinked fibrous collagen and crosslinked fibrous collagen.

In addition, in the joining member of the present embodiment, the fibrous collagen preferably forms a collagen fiber bundle as shown in FIGS. 1 to 5 described below.

In the joining member of the present embodiment, a content of the non-crosslinked fibrous collagen in the fibrous collagen can be appropriately selected according to a type of a tissue to be joined. The content of the non-crosslinked fibrous collagen in the fibrous collagen is preferably 50% by mass or more, more preferably 70% by mass or more, further preferably 90% by mass or more, particularly preferably 95% by mass or more, and most preferably 100% by mass, based on a total mass of the fibrous collagen.

By setting the content of the non-crosslinked fibrous collagen in fibrous collagen to the lower limit or more, it is possible to relax and expand a more sufficient amount of non-crosslinked fibrous collagen and to more effectively fit collagen fibers in a living tissue. Thereby, a living tissue can be joined more reliably. In addition, elasticity of the joined collagenous tissue can be maintained.

As fibrous collagen used for the joining member of the present embodiment, an atelocollagen is preferable because of low antigenicity and high biocompatibility thereof. In addition, a type of the fibrous collagen may be any of type I, type II, and type III fibrous collagen. These fibrous collagens may be used alone or in combination of two or more types. In addition, the type of the fibrous collagen can be appropriately selected according to a type of a collagen tissue to be joined.

The joining member of the present embodiment preferably has a shape having a certain area in order to cover a joined portion of the tissue, and can be film-like, sheet-like, or sponge-like. A size of the joining member can be appropriately adjusted to match a surface area of the joined portion.

Further, in the present description, "film" means a film-like shape having a thickness of less than 250 μm, and "sheet" means a thin plate-like shape having a thickness of 250 μm or more. In addition, "sponge" means a structure that is thicker than the sheet, has more voids than the sheet, has a low density, and has a high elasticity. A thickness of a sponge-like joining member is approximately 1 cm or more, but is not limited thereto.

In addition, the "thickness" as used herein means a thickness of an entire film-like joining member, an entire sheet-like joining member or an entire sponge-like joining member, and for example, a thickness of a film-like joining member, a sheet-like joining member or a sponge-like joining member formed of a plurality of layers means a total thickness of all the layers constituting the film-like joining member, the sheet-like joining member, or the sponge-like joining member.

In addition, the thickness of the joining member of the present embodiment can be, for example, 1 μm or more and 10 cm or less.

In addition, the joining member of the present embodiment substantially does not contain water. That is, it means that the fibrous collagen contained in the joining member of the present embodiment is not a gelatin.

The phrase "substantially does not contain water" as used herein means a state of not containing water at all. Alternatively, the phrase means a state of containing a very small amount of water to an extent that the non-crosslinked fibrous collagens do not fit together when portions of the non-crosslinked fibrous collagen contained in one joining member of the present embodiment are overlapped and heated, or non-crosslinked fibrous collagens contained in two joining member of the present embodiment are layered and heated so as to overlap with each other. As a result, it is possible to prevent the fibrous collagens contained in the joining member of the present embodiment from being fitted to each other at the time of storage under a high-temperature environment.

<<Laminate Body>>
<Structure of Laminate Body>

The structure of the laminate body of the present embodiment will be described below in detail with reference to the drawings.

FIG. 1 is a bottom view showing an example of a laminate body of the present embodiment. In addition, FIG. 2 is a cross-sectional view showing an example of the laminate body of the present embodiment.

A laminate body 10 shown in FIGS. 1 and 2 includes a joining member 1, a first adhesive layer 2 and a support 3.

The joining member 1 is layered on one surface of the support 3, and the first adhesive layer 2 is layered on the same surface as the surface of the support 3 on which the joining member 1 is layered, in a region on which the joining member 1 is not layered. The joining member 1 includes a collagen fiber bundle in which a fibrous collagen is bundled. In addition, this collagen fiber bundle includes a non-crosslinked fibrous collagen.

In addition, by providing the first adhesive layer 2 and the support 3, the laminate body 10 can be pressed and fixed to a joined portion of a tissue. As a result, the joining member 1 can be brought into close contact with the tissue with a constant pressure being applied to the tissue.

In addition, the laminate body of the present embodiment may further include a second adhesive layer between the support and the joining member. As described below, the second adhesive layer can be easily peeled off from the joining member.

FIG. 3 is a cross-sectional view showing an example of a laminate body of the present embodiment. Further, in drawings subsequent to FIG. 3, the same components as those shown in the already described drawings are denoted by the same reference numerals as those in the already described drawings, and the detailed description thereof will be omitted.

A laminate body 20 shown in FIG. 3 is the same as the laminate body 10 shown in FIG. 2 except that a second adhesive layer 4 is provided between the support 3 and the joining member 1. That is, the laminate body 20 includes the joining member 1, the first adhesive layer 2, the support 3 and the second adhesive layer 4. In addition, the joining member 1, the second adhesive layer 4, and the support 3 are layered in this order. Further, the first adhesive layer 2 is layered on the same surface as the surface of the support 3 on which the joining member 1 and the second adhesive layer 4 are layered, in a region on which the joining member 1 and the second adhesive layer 4 are not layered.

In addition, by providing the second adhesive layer 4, the joining member 1 can be fixed onto the support 3 until the support 3 and the first adhesive layer 2 are removed.

In addition, in the laminate body of the present embodiment, the support or the second adhesive layer may include, at least in part, a temperature-sensitive material configured to allow naked eyes or a sensor to sense that the joined portion has reached an optimum temperature (less than 60° C. and greater than body temperature).

FIG. 4 is a cross-sectional view showing an example of a laminate body of the present embodiment.

A laminate body 30 shown in FIG. 4 is the same as the laminate body 10 shown in FIG. 2 except that the support 3 includes a temperature-sensitive material-containing layer 5 in a part thereof. That is, the laminate body 30 includes the joining member 1, the adhesive layer 2, and the support 3. The joining member 1 is layered on one surface of the support 3. The first adhesive layer 2 is layered on the same surface as the surface of the support 3 on which the joining member 1 is layered, in a region on which the joining member 1 is not layered. Further, the support 3 includes the temperature-sensitive material-containing layer 5 in a part thereof. In a case of joining a living tissue using the laminate body 30, the laminate body is adhered with the temperature-sensitive material-containing layer 5 in the support 3 being arranged so as to be aligned with a joined portion, so that it can be sensed by the naked eyes or the sensor that the joined portion has reached an optimum temperature (less than 60° C. and greater than body temperature).

FIG. 5 is a cross-sectional view showing an example of a laminate body of the present embodiment.

A laminate body 40 shown in FIG. 5 is the same as the laminate body 20 shown in FIG. 3 except that the second adhesive layer 4 includes the temperature-sensitive material-containing layer 5 in a part thereof. That is, the laminate body 40 includes the joining member 1, the first adhesive layer 2, the support 3, and the second adhesive layer 4. In addition, the joining member 1, the second adhesive layer 4, and the support 3 are layered in this order. In addition, the first adhesive layer 2 is layered on the same surface as the surface of the support 3 on which the joining member 1 and the second adhesive layer 4 are layered, in a region on which the joining member 1 and the second adhesive layer 4 are not layered. Further, the second adhesive layer 4 includes the temperature-sensitive material-containing layer 5 in a part thereof. In a case of joining a living tissue using the laminate body 40, the laminate body is adhered with the temperature-sensitive material-containing layer 5 in the second adhesive layer 4 being arranged so as to be aligned with a joined portion, so that it can be sensed by the naked eyes or the sensor that the joined portion has reached an optimum temperature (less than 60° C. and greater than body temperature).

The laminate body of the present embodiment is not limited to those shown in FIGS. 1 to 5, and in a range in which the effect of the laminate body of the present embodiment is not impaired, some configurations of those shown in FIGS. 1 to 5 may be changed or deleted, or other configurations may be further added to those described above.

For example, the layered bodies shown in FIGS. 1 to 5 have rectangular planar shapes, but other shapes can also be used. Examples of a planar shape of the laminate body include, but are not limited to, a polygonal shape (including a regular polygon shape or the like), a semicircular shape, an elliptical shape, a substantially circular shape, and the like.

In addition, for example, in the laminate body shown in FIG. 4, a thickness of the temperature-sensitive material-containing layer 5 is the same as a thickness of the support 3, but the thickness of the temperature-sensitive material-containing layer 5 may be smaller than the thickness of the support 3. Alternatively, either the support 3 or the second adhesive layer 4 may include the temperature-sensitive material-containing layer 5. Alternatively, the temperature-sensitive material-containing layer 5 may be provided between the support 3 and the joining member 1, between the joining member 1 and the second adhesive layer 4, between the second adhesive layer 4 and the support 3 or on the support 3.

<Components of Laminate Body>

Next, each component constituting the laminate body will be described in detail below.

[First Adhesive]

An adhesive forming the first adhesive layer is only required to show no toxicity to a living body. A type of the adhesive can be appropriately selected according to a type of a tissue to be adhered and a material of the support.

Examples of the first adhesive include, but are not limited to, an adhesive made of a synthetic compound, an adhesive made of a natural compound, a double-sided tape, and the like.

Examples of the adhesive made of the synthetic compound include an urethane adhesive, a cyanoacrylate adhesive, a polymethyl methacrylate (PMMA), a calcium phosphate adhesive, a resin cement, and the like.

Examples of the adhesive made of the natural compound include fibrin glue, gelatin glue, and the like.

As the double-sided tape, tapes used in medical applications or the like are suitably used. In addition, examples of the double-sided tape include tapes having a structure in which an adhesive is layered on both sides of a supporting tape. Examples of the adhesive used for the double-sided tape include a known adhesive which is rubber-based, acrylic-based, urethane-based, silicone-based, or vinyl ether-based, or the like.

More specific examples of the double-sided tape include, a double-sided tape for attachment to skin manufactured by 3M Japan Ltd. (product numbers: 1510, 1504 XL, 1524, and the like), a double-sided adhesive tape for skin manufactured by Nitto Denko Corporation (product numbers: ST 502, ST 534, and the like), a double-sided medicinal tape manufactured by Nichiban Medical Corp. (product numbers: #1088, #1022, #1010, #809SP, #414125, #1010R, #1088R, #8810 R, #2110 R, and the like), a thin type foam based double-sided adhesive tape manufactured by DIC Corp. (product numbers: #84010, #84015, #84020, and the like), and the like.

The first adhesive layer may be formed of one type among those exemplified above, or may be formed of two or more types.

A thickness of the first adhesive layer can be, for example, 1 μm or more and 1000 μm or less.

Further, the "thickness of the first adhesive layer" as used herein means a thickness of the entire first adhesive layer, and for example, a thickness of a first adhesive layer formed of a plurality of layers means a total thickness of all the layers constituting the first adhesive layer.

[Second Adhesive]

A second adhesive forming the second adhesive layer is only required to show no toxicity to a living body, have low adhesiveness to a fibrous collagen, and have high adhesiveness to the support. By using such a second adhesive, the support can be attached to and detached from the fibrous collagen.

Such a second adhesive can be appropriately selected from those exemplified in "First adhesive" according to the type of material constituting the support.

[Support]

A material of the support is only required to show no toxicity to a living body, and have low adhesiveness to a collagen. In addition, in a case of using a laser in a "heating step" of a "method for using the joining member or the laminate body" described below, the material of the support is preferably a material that transmits the laser. Examples of the material of the support include, but are not limited to, an elastomer material, a plastic containing a dendritic polymer, a copolymer, and the like.

Examples of the elastomer material include urethane rubber, nitrile rubber, silicone rubber, silicone resin (for example, polydimethylsiloxane), fluororubber, acrylic rubber, isoprene rubber, ethylene propylene rubber, chlorosulfonated polyethylene rubber, epichlorohydrin rubber, chloroprene rubber, styrene butadiene rubber, butadiene rubber, polyisobutylene rubber, and the like.

Examples of the dendritic polymer include polyvinyl chloride, polyvinyl alcohol, polymethyl methacrylate, polydimethylsiloxane monomethacrylate, cyclic olefin polymer, fluorocarbon polymer, polytetrafluoroethylene (Teflon (registered trademark)), polystyrene, polypropylene, polyethyleneimine, and the like.

Examples of the copolymer include polyvinyl acetate-co-maleic anhydride, polystyrene-co-maleic anhydride, polyethylene-co-acrylic acid, derivatives thereof, and the like.

The support may be formed of one type among materials exemplified above, or may be formed of two or more types.

A thickness of the support can be, for example, 1 μm or more and 2000 μm or less.

Further, the "thickness of the support" as used herein means the thickness of the entire support, and for example, a thickness of a support formed of a plurality of layers means a total thickness of all the layers constituting the support.

[Temperature-Sensitive Material]

The temperature-sensitive material is used to sense, by the naked eyes or the sensor, that the joined portion has reached the optimum temperature (less than 60° C. and greater than body temperature) by heating. Examples of the temperature-sensitive material include a thermochromic pigment, and the like.

The thermochromic pigment may be a reversible pigment that decolorizes (or whitens) when the temperature rises to the optimum temperature and develops color when the temperature drops below the optimum temperature, and may be a reversible pigment that develops color when the temperature rises to the optimum temperature and decolorizes (or whitens) when the temperature drops below the optimum temperature.

Examples of compounds constituting the thermochromic pigment include inorganic compounds such as $Ag_2HgI_4$ and $Cu_2HgI_4$.

In addition, examples of a color in a colored state of the thermochromic pigment include, blue, violet, black, red, rose red, green, emerald green and the like.

Examples of commercially available thermochromic pigments include, but are not limited to, pigments having a color erasing start of 30° C. or higher and 50° C. or lower, an intermediate color setting temperature of 35° C. or higher and 55° C. or lower, and a color erasing completion of 40°

C. or higher and 60° C. or lower, among OR series, DR series and ER series manufactured by Kirokusozai Sogo Kenkyusho Co. The thermochromic pigment may be composed of one type among those exemplified above, or may be composed of two or more types.

A thickness of a temperature-sensitive material-containing layer can be, for example, 100 nm or more and 1000 μm or less.

Further, the "thickness of a temperature-sensitive material-containing layer" as used herein means the thickness of the entire temperature-sensitive material-containing layer, and for example, a thickness of a temperature-sensitive material-containing layer formed of a plurality of layers means a total thickness of all the layers constituting the temperature-sensitive material-containing layer.

[Method for Using Joining Member or Laminate Body]

Next, the method for using the joining member or the laminate body of the present embodiment will be described below in detail with reference to the drawings.

FIG. 6 is a schematic process view showing an example of a method for using the joining member or the laminate body of the present embodiment.

The method for using the joining member or the laminate body of the present embodiment includes a heating step and a cooling step. Each step will be described in detail below.

[Heating Step]

In the heating step, the joining member or the laminate body, which is layered on a tissue, is heated to less than 60° C. and greater than body temperature.

Specifically, as shown in FIG. 6, in order to join a collagenous tissue 100 of a living body in a living tissue such as skin, first, the joining member 1 (laminate body 10) is adhered onto a cut portion of the collagen tissue 100 of the living body. Next, the joining member 1 (laminate body 10) is heated. At this time, it is estimated that, first, the temperature of moisture in the collagenous tissue of the cut living body rises, so that the temperature of the collagenous tissue of the cut living body rises, and then, the temperature of the adhered joining member 1 (laminate body 10) rises to a similar temperature.

A lower limit of a heating temperature can be higher than body temperature. Body temperature can be appropriately selected according to an animal species to be joined.

For example, when the animal species to be joined is a thermophilic animal such as fish, amphibian and reptile, body temperature is appropriately adjusted according to an ambient temperature.

Therefore, when the animal species to be joined is fish, amphibian and reptile, the lower limit of the heating temperature can be 4° C., preferably 10° C., more preferably 15° C., and further preferably 20° C.

In addition, for example, when the animal species to be joined is bird, body temperature is about 40° C. or higher and 43° C. or lower.

Therefore, when the animal species to be joined is bird, the lower limit of the heating temperature can be 43° C., preferably 45° C., and more preferably 47° C.

In addition, for example, when the species of the animal to be joined is human, body temperature is about 35° C. or higher and 39° C. or lower.

Therefore, when the animal species to be joined is human, the lower limit of the heating temperature can be 39° C., preferably 40° C., more preferably 42° C., further preferably 45° C., and particularly preferably 47° C.

In addition, for example, when the animal species to be joined is mammal other than human, body temperature is about 36° C. or higher and 42° C. or lower.

Therefore, when the animal species to be joined is mammal other than human, the lower limit of the heating temperature can be 42° C., preferably 45° C., and more preferably 47° C.

Meanwhile, an upper limit of the heating temperature can be less than 60° C., preferably 55° C. or lower, and more preferably 52° C. or lower.

That is, when the animal species to be joined is human, the heating temperature can be set to be greater than 39° C. and less than 60° C., preferably 40° C. or higher and 55° C. or lower, more preferably 42° C. or higher and 55° C. or lower, further preferably 45° C. or higher and 55° C. or lower, and particularly preferably 47° C. or higher and 52° C. or lower.

By setting the heating temperature to the lower limit or more, the collagen fibers can be more effectively relaxed and expanded. Meanwhile, by setting the heating temperature to the upper limit or less, it is possible to more effectively prevent tissue components of a living tissue from being denatured and destroyed. This makes it possible to more effectively prevent tissue disorders of the living tissue.

In addition, the heating method is only required to non-invasively heat a joined portion in the temperature range in a short time, and examples thereof include a heating method using a laser, an RF wave dielectric heating method, an RF wave electromagnetic induction heating method, a microwave heating method, an ultrasonic heating method and the like. Among them, as the heating method, a heating method using a laser is preferable because it can heat a local portion to a target temperature in a short time in a non-contact manner. In a case of heating using a laser, a wavelength can be set to, for example, about 350 nm or more and 6000 nm or less, for example, about 400 nm or more and 4000 nm or less, for example, about 1470 nm or more and 1950 nm or less. In addition, in the case of heating using a laser, a heating time can be set to a short time of, for example, about 1 second or more and 60 seconds or less.

In addition, in the heating step, it is preferable to heat while pressing the joined portion. This makes it possible to more effectively fit the collagen fibers in the living tissue and the non-crosslinked fibrous collagen contained in the joining member. Examples of a method for pressing the joined portion include a method for fixing the laminate body to a surrounding tissue of the living tissue by using a laminate body including a support, a joining member, and a first adhesive layer.

[Cooling Step]

In the cooling step, the heated joining member or laminate body is cooled.

An upper limit of a cooling temperature can be body temperature or lower. A lower limit of the cooling temperature can be a lower limit of body temperature of the animal species to be joined. Body temperature can be appropriately selected according to the animal species to be joined. Body temperature of each animal species is as exemplified in the "heating step".

For example, when the animal species to be joined is fish, amphibian and reptile, the cooling temperature can be 20° C. or lower, and preferably 0° C. or higher and 15° C. or lower.

In addition, for example, when the animal species to be joined is bird, the cooling temperature can be 43° C. or lower, and preferably 40° C. or higher and 43° C. or lower.

In addition, for example, when the animal species to be joined is human, the cooling temperature can be 39° C. or lower, and preferably 35° C. or higher and 38° C. or lower.

In addition, for example, when the animal species to be joined is mammal other than human, the temperature can be 42° C. or lower, and preferably 36° C. or higher and 42° C. or lower.

By setting the cooling temperature in the temperature range, the collagen fibers in the living tissue and the non-crosslinked fibrous collagen contained in the joining member can be contracted and tightened while maintaining the fitted state, and the collagen fibers can be joined to each other. Therefore, it is possible to join the living tissue by using the joining member and the laminate body of the present embodiment.

In addition, examples of a cooling method include a method of standing at room temperature, a method of applying cool air to the joined portion, a body surface cooling method using such as a Peltier element, a compressed gas, an ice bag, a cooling blanket, an ice water tank, or the like.

<Application>

The joining member and the laminate body of the present embodiment may be used for joining a living tissue, or may be used for joining a living tissue and an artificial object.

That is, in one embodiment, the present invention provides a method for joining a living tissue using the joining member or the laminate body. In addition, in one embodiment, the present invention provides a method for joining a living tissue and an artificial object using the joining member or the laminate body.

The joining member and the laminate body of the present embodiment are preferably used in joining of nerves (peripheral nerves, central nerves, and the like), organs (liver, pancreas, and the like), bones, teeth, a tissue without blood flow (cartilage, meniscus, and the like), or the like. In addition, by using the joining member and the laminate body of the present embodiment, it is possible to reconstruct tissue in a state in which tissue fusion is difficult due to arteriosclerosis, inflammation, ischemia, and the like. In addition, for example, hemostasis and reconstruction can be easily achieved in a state in which anastomosis is difficult in endoscopic surgery. In addition, for example, it is preferably used for joining a living tissue and an artificial organ or an implant device. Examples of the artificial organ or the implant device include artificial skin, cochlear implants, pacemakers, bone plates and the like. In addition, for example, it is possible to reconstruct minute blood vessels and lymphatic vessels of 1 mm or less. In addition, for example, by using the joining member and the laminate body of the present embodiment as a reinforcing material in joining of living tissue by a staple used in the conventional surgery, it is possible to perform anastomosis with higher reliability.

<<Treatment System>>

The treatment system of the present embodiment includes the joining member according to the embodiment or the laminate body according to the embodiment, and a heating unit.

According to the treatment system of the present embodiment, it is possible to join a living tissue without causing degeneration and destruction of tissue components of a living tissue. That is, a living tissue can be joined without bleeding, hardening, dehydration, carbonization or the like caused by tissue damage.

Next, each component of the treatment system of the present embodiment will be described in detail below.

<Heating Unit>

The heating unit is only required to be configured to heat the joining member or the laminate body to less than 60° C. and greater than body temperature. Specific examples of the heating unit include a laser, an RF wave generator (dielectric and induction), a microwave generator, an ultrasonic generator and the like. Among them, as the heating unit, a laser is preferable because it can instantaneously heat a local area.

<Temperature Control Unit>

The treatment system of the present embodiment may further include a temperature control unit.

The temperature control unit is only required to be configured to control the heating unit such that the temperature of the joining member or the laminate body heated by the heating unit becomes less than 60° C. and greater than body temperature. The temperature control unit can include, for example, a thermometer or a temperature sensor and a control circuit. In addition, the thermometer or the temperature sensor and the heating unit can be connected to the control circuit. Thereby, the temperature of the joining member or the laminate body heated by the heating unit can be sensed by using the thermometer or the temperature sensor, and heating by the heating unit can be terminated by the control circuit when the temperature detected by the thermometer or the temperature sensor falls within a temperature range less than 60° C. and greater than body temperature.

In addition, when the laminate body includes a thermochromic pigment, a sensor for identifying a change in color of the thermochromic pigment may be provided in place of the thermometer or the temperature sensor. At this time, the sensor and the heating unit can be connected to the control circuit. Thereby, the change in color of the thermochromic pigment in the laminate body heated by the heating unit can be detected by using the sensor, and when the color of the thermochromic pigment is decolorized or colored at the temperature range less than 60° C. and greater than body temperature, the sensor identifies the change in color, so that the heating by the heating unit can be terminated by the control circuit.

<Other Components>

The treatment system of the present embodiment may further include a cooling unit in addition to the components. Examples of the cooling unit include a Peltier element, a compressed gas, a cold air generation device, an ice bag, a cooling blanket, an ice water tank, and the like.

In addition, when the cooling unit is provided, the temperature control unit may control the cooling unit such that the temperature of the joining member or the laminate body heated by the heating unit becomes less than body temperature.

In addition, the treatment system of the present embodiment may further include a fixing portion in addition to the components. The fixing portion is only required to be configured to fix the joining member or the laminate body at a desired position so as not to peel off, and examples thereof include a clamp and a surgical tape.

<Using Method>

The treatment system of the present embodiment can be used, for example, in the following procedure. First, the joining member or the laminate body is adhered onto a living tissue to be joined. Then, by using the fixing portion or the like, the joining member or the laminate body is fixed and adhered on the living tissue, further, the temperature control unit heats the joining member or the laminate body by using the heating unit while detecting the temperature, and relaxes and expands the collagen fibers in the living tissue and the non-crosslinked body contained in the joining member or the laminate body to fit them. Next, when the temperature of the joining member or the laminate body is in a range less than 60° C. and greater than body temperature, the heating of the joining member or the laminate body by the heating unit is terminated by the temperature control unit or the like. Then, by cooling the joining member or the laminate body to body temperature or lower using the cooling unit or the like, the collagen fibers in the living tissue and the non-crosslinked fibrous collagen contained in the joining member or the laminate body can be contracted and tightened while maintaining the fitted state, and the collagen fibers can be joined to each other. Therefore, it is possible to join the living tissues by using the treatment system of the present embodiment.

A vertebrate is preferable as an application object of the treatment system of the present embodiment. Examples of a vertebrate include fish, amphibian, reptile, bird, mammal, and the like. Among them, mammalian is preferable. Examples of mammalian include, but are not limited to, human, chimpanzee and other primates; and domestic animals, pet animals, and laboratory animals such as dog, cat, rabbit, horse, sheep, goat, cow, pig, rat (including nude rat), mouse, (including nude mouse and SCID mouse), and marmot. Among them, human is preferable as mammalian.

EXAMPLE

Hereinafter, the present invention will be described with reference to examples, but the present invention is not limited to the following examples.

[Reference Example 1] Test for Confirming Temperature Change of Bovine Carotid Artery Adventitia A temperature change of collagen in a bovine carotid artery adventitia was observed. Specifically, a bovine carotid artery was allowed to stand for 48 hours in a fixative (glutaraldehyde) at 4° C. and 45° C.

Next, a state of the collagen in the bovine carotid artery adventitia was observed using a scanning electron microscope (manufactured by Hitachi High-Technologies Corporation, magnification: 30,000 times). The result is shown in FIG. 7. In FIG. 7, a left image shows a result of keeping the temperature at 4° C., and a right image shows the result of keeping the temperature at 45° C.

From FIG. 7, it was confirmed that a binding state of the collagen fiber bundle in the bovine carotid artery adventitia kept warm at 4° C. was maintained, but the collagen fiber bundle in the bovine carotid artery adventitia kept warm at 45° C. was relaxed and expanded. It is presumed that this is because the collagen fiber bundle in the living tissue is non-crosslinked, and thus was relaxed and expanded by heating to a temperature of about 45° C.

[Example 1] Joining Test of Bovine Carotid Artery

1. Joining Test of Bovine Carotid Artery

Then, apart of a bovine carotid artery was cut, and was subjected to a joining test using the laminate body. A procedure of the joining test is shown in FIG. 8. Specifically, first, all layers of a half circumference of a bovine carotid artery having an outer diameter of about 8 mm were incised, and both ends of a layer of blood vessel were matched and brought into close contact with each other. Then, a biomaterial collagen (manufactured by Koken Co., Ltd., content of non-crosslinked atelocollagen fibers in atelocollagen fibers: 90% by mass or more) was used to cover an arterial adventitia-deficient portion of an incision portion, and a Teflon sheet was wound on the arterial adventitia-deficient portion and pressure-bonded. Then, the incision portion was irradiated with a laser (wavelength: 1950 nm, fiber laser) set at a maximum temperature of 55° C. for 2 seconds, and cooled to about 37° C. (hereinafter, the bovine carotid artery subjected to the treatment may be referred to as "Group A"). In addition, as a control group, a bovine carotid artery in which a biomaterial collagen was used to cover the arterial adventitia-deficient portion of the incision portion, and a Teflon sheet was wound on the arterial adventitia-deficient portion and pressure-bonded, but laser irradiation was not performed (hereinafter, the bovine carotid artery subjected to the treatment may be referred to as "Group B"), and a bovine carotid artery in which laser irradiation was performed without covering the incision portion with a biomaterial collagen (hereinafter, the bovine carotid artery subjected to the treatment may be referred to as "Group C") were also prepared.

2. Observation of Joined Portion

Then, a tissue piece of a cross section of the joined portion of each bovine carotid artery in Groups A to C obtained in "1." was prepared, and for some of the tissue pieces, Masson's Trichrome staining was used to stain the biomaterial collagen red and the collagen fiber bundle in the bovine carotid adventitia into a blue color. Observation was performed using an optical microscope (manufactured by Carl Zeiss, magnification: 400 times) and a scanning electron microscope (manufactured by Hitachi High-Technologies Corporation, magnification: 30,000 times), and comparative examination was performed. Representative results for Group A are shown in FIG. 9. Two upper images in FIG. 9 are optical microscope images, where a left image is a bright field image, and a right image is a stained image. In addition, three lower images in FIG. 9 are electron microscope images, where a left image corresponds to a biomaterial collagen portion. A middle image corresponds to a fitting portion between the biomaterial collagen and the collagen fiber bundle in the bovine carotid artery adventitia. A right image corresponds to the collagen fiber bundle portion in the bovine carotid artery adventitia.

3. Pressure Resistance Test

In addition, a pressure resistance test was performed using each bovine carotid artery adventitia of Groups A to C obtained in "1.". Specifically, the pressure resistance of the incision portion when each bovine carotid artery was perfused with liquid was measured. The results are shown in FIG. 10 and Table 1 below.

TABLE 1

| | Collagen | Heating by laser | Pressure resistance (average value) [mmHg] |
|---|---|---|---|
| Group A | + | + | 303.6 ± 55.2 |
| Group B | + | − | 50.8 ± 33.0 |
| Group C | − | + | 49.0 ± 11.8 |

From the lower middle image of FIG. 9, in Group A, in the fitting portion, fibers having no striped patterns derived from the biomaterial collagen and fibers having striped patterns derived from the collagen in the bovine carotid artery adventitia were entangled with each other, and tissue joining can be confirmed. Meanwhile, in Group B and Group C, tissue joining could not be confirmed (not shown).

In addition, from FIG. 10 and Table 1, the pressure resistance at the incision portion was significantly higher in Group A (P<0.0001).

[Example 2] Collagen Fitting Test in Intestinal Perforation Model

A perforation model having a diameter of about 3 mm was prepared in a small intestine of a pig. Then, a perforation portion was covered with a biomaterial collagen having a length of 10 mm×a width of 10 mm×a thickness of 0.3 mm (manufactured by Koken Co., Ltd., content of non-crosslinked atelocollagen fibers in atelocollagen fibers: 50% by mass or more), wound by a Teflon sheet and pressure-bonded, and then irradiated with a semiconductor laser (wavelength: 1400 to 1950 nm, fiber laser) set to a maximum temperature of 52° C. for 10 seconds and cooled to about room temperature (15° C. or higher and 35° C. or lower) (hereinafter, the small intestine of a pig subjected to the treatment may be referred to as "Group A"). In addition, a small intestine of a pig in which a perforation portion was sutured and closed (hereinafter, the small intestine of a pig subjected to the treatment may be referred to as "Group B") was prepared as well.

For the obtained Groups A and B, using the same method as described in Example 1, collagen morphology was observed with an optical microscope and a scanning electron microscope, and a pressure resistance test was performed.

As a result, an average maximum pressure resistance was 145±21 mmHg in Group A (n=5), but was 65±14 mmHg in Group B (n=5), where Group A was significantly higher (p<0.0001). In addition, similar to the microscopic image of Group A of Example 1, in a microscopic image of Group A, it was observed that two types of collagen fibers, one having no striped patterns derived from the biomaterial collagen, and one having striped patterns derived from the collagen in the small intestine of a pig, were entangled with each other (not shown).

From the above, it is shown that by using the laminate body of the present embodiment, it is possible to join the living tissue without causing degeneration and destruction of the tissue components of the living tissue. In addition, in the joined living tissue, no tissue disorder was observed, and appropriate elasticity was maintained.

INDUSTRIAL APPLICABILITY

According to the joining member and the laminate body of the present embodiment, it is possible to join a living tissue without causing a tissue disorder. The joining member and the laminate body of the present embodiment are preferably used in joining such as nerves (peripheral nerves, central nerves, and the like), bones, and tissues without blood flow (cartilage, meniscus, and the like).

REFERENCE SIGNS LIST

1 joining member; 2 first adhesive layer; 3 support; 4 second adhesive layer; 5 temperature-sensitive material-containing layer; 10, 20, 30, 40 laminate body; 100 collagenous tissue of a living body

The invention claimed is:

1. A laminate body, comprising:
   a support;
   a tissue-joining member comprising a non-crosslinked fibrous collagen, which is layered on one surface of the support; and
   a first adhesive layer that is layered on said one surface of the support in a region on which the tissue-joining member is not layered.

2. The laminate body according to claim 1, wherein the tissue-joining member is film-like, sheet-like, or sponge-like.

3. The laminate body according to claim 1, wherein the tissue-joining member does not comprise water.

4. The laminate body according to claim 1, wherein the non-crosslinked fibrous collagen is an atelocollagen.

5. The laminate body according to claim 1, further comprising a second adhesive layer that is layered between the support and the tissue-joining member.

6. The laminate body according to claim 5, wherein the support or the second adhesive layer comprises a temperature-sensitive material at least in a part thereof.

7. A method for using the laminate body according to claim 1, the method comprising:
   heating the laminate body layered on a tissue to less than 60° C. and greater than body temperature; and
   cooling the laminate body to body temperature or lower.

8. A treatment system comprising:
   the laminate body according to claim 1; and
   a heating unit.

9. The treatment system according to claim 8, further comprising a temperature control unit configured to control the heating unit such that a temperature of the laminate body heated by the heating unit is less than 60° C. and greater than body temperature.

10. The treatment system according to claim 8, wherein the heating unit is a laser.

11. A method comprising:
    heating a tissue-joining member layered on a tissue to less than 60° C. and greater than body temperature, the tissue-joining member comprising a non-crosslinked fibrous collagen; and
    cooling the heated joining member to body temperature or lower.

12. A treatment system comprising:
    a tissue-joining member comprising a non-crosslinked fibrous collagen;
    a heating unit; and
    a temperature control unit configured to control the heating unit such that a temperature of the tissue-joining member heated by the heating unit is less than 60° C. and greater than body temperature.

13. A treatment system comprising:
    a tissue-joining member comprising a non-crosslinked fibrous collagen; and
    a heating unit, wherein the heating unit is a laser.

* * * * *